United States Patent [19]

Jolly

[11] Patent Number: Plant 5,552

[45] Date of Patent: Sep. 10, 1985

[54] NEW ROSE PLANT—HOMBRE

[75] Inventor: Nelson F. Jolly, Galena, Md.

[73] Assignee: Jolly's Rosehill Farm of Kent, Inc., Galena, Md.

[21] Appl. No.: 564,286

[22] Filed: Dec. 22, 1983

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new miniature rose variety of near white and Spanish orange coloring long lasting on the plant and as a cut flower.

1 Drawing Figure

The present invention relates to a new and distinct variety of rose plant of the miniature rose class, which was originated by my crossing as seed parent the rose known as "Humdinger" (U.S. Plant Pat. No. 4,294) and the rose known as "Rise 'N Shine" (U.S. Plant Pat. No. 4,231) as pollen parent. The varietal denomination of this new variety is "Hombre".

Among the novel characteristics possessed by this new variety which distinguish it from its parents and all other varieties of which I am aware are its exceptionally heavy petaled flowers of grand form which are long lasting on the plant and as cut flowers combining near white outer petal coloring with Spanish orange tonality at centers where petals remain bunched. Asexual reproduction by budding of the new variety as performed in Kent County, Md., shows that the foregoing and other distinguishing characteristics come true to form and are established and transmitted through succeeding propagations.

The accompanying drawings show typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementiond color charts, e.g., "25D" is plate 25D of The Royal Horticultural Society Colour Chart.

Parentage: Seedling.

*Seed parent.*—"Humdinger".

*Pollen parent.*—"Rise 'N Shine".

Class: Miniature.

The following observations are made of specimens grown indoors in Kent County, Md., during the month of August.

FLOWER

Blooming habit: Continuous.

A. Bud:

(1) *Size.*—Small.

(2) *Form.*—Urn shaped as petals unfurl.

(3) *Color.*—When sepals first divide — Nasturtium orange 25D. When petals begin to unfurl — Color of Petal undersurface is near 24C to 24D (tangerine orange).

(4) *Sepals.*—As long as bud.

(5) *Peduncle.*—Length — About 1 inch. Aspect — Straight. Strength — Erect. Color — Near 144A.

B. Bloom:

(1) *Size.*—Average size when fully expanded — about $1\frac{1}{2}$ inches.

(2) *Borne.*—Singly.

(3) Form.—High centered at first, becoming flat, petals reflex upon opening; flower maintains symmetrical exhibition form.

(4) *Petalage.*—Number of petals under normal conditions — about 60 to 65.

(5) *Color.*—As sepals fall and petals begin to unfurl orange coloring of petal undersurface, Nasturtium orange to tangerine orange, is first seen. Upon further opening flower coloring appears in a variety of hues ranging from white or near white with a pinkish cast, approaching 36D, to near white with slight orange cast, approaching 27D. Coloring of flower centers where petals bunch emphasizes orange tonality near Spanish orange 26C to 26D. Flowers at $\frac{1}{3}$ to $\frac{1}{2}$ open stage combine near white coloring of petal top surface of unfurled outer petals with orange toned flower centers where petals remain bunched in this heavily petaled cultivar.

C. Petals:

(1) *Texture.*—Medium.

(2) *Appearance.*—Inside — velvety, outside — velvety.

(3) *Form.*—Fan shaped, some with pointed apices.

(4) *Arrangement.*—Regularly arranged, shingle-like.

(5) *Petaloids in center.*—Few.

(6) *Persistence.*—Persistent.

(7) *Fragrance.*—Slight.

(8) *Lasting quality.*—Very long lasting on plant and as cut flower about one week.

REPRODUCTIVE ORGANS

A. Stamens, filaments and anthers:

(1) *Arrangement.*—Regularly arranged around styles.

(2) *Color.*—Orange yellow.

B. Pollen:

*Color.*—Orange yellow.

C. Styles: Uneven length.

D. Stigmas:

*Color.*—Near 40B.

E. Hips: None observed.

PLANT

A. Form: Spreading.

B. Growth: Very vigorous, uniform branching.
*Height attained.*—About 12 to 18 inches.

C. Foliage: Compound 5 leaflets.
(1) *Size.*—Small.
(2) *Quantity.*—Abundant.
(3) *Color.*—New foliage: Upper side — Near to 144A. Under side — Near to 138C. Old foliage: Upper side — Near 137A. Under side — Near 138B.
(4) *Shape.*—Oval, pointed.
(5) *Texture.*—Upper side is slightly glossy and under side is dull.
(6) *Edge.*—Serrated.
(7) *Serration.*—Serrulate.
(8) *Leaf stem.*—Color — Near to 138A. Under side — Near 138A.
(9) *Stipules.*—Medium.
(10) *Resistance to disease.*—Blackspot — Good. Mildew — Good.

D. Wood:

(1) *New wood.*—Color — Near 144B. Bark — Smooth.
(2) *Old wood.*—Color — Near 137A. Bark — Smooth.

E. Thorns:
(1) *Thorns.*—Quantity (main stalk): Ordinary. On laterals from stalk — few. Form — Long, straight, thin. Length — Medium. Color — Near 144B. Position — Irregular.
(2) *Prickles.*—Few.

F. Winter hardiness. Requires ordinary protection in extreme climates.

I claim:

1. A new and distinct variety of rose plant of the miniature rose class, substantially as shown and described, characterized particularly by exceptionally heavy petaled flowers borne primarily one to a stem of good form with petals reflexing upon opening while retaining symmetrical configuration and flowers which are very long lasting on the plant and after cutting which flowers combine near white coloring of outer petals with Spanish orange flower centers where petals remain bunched.

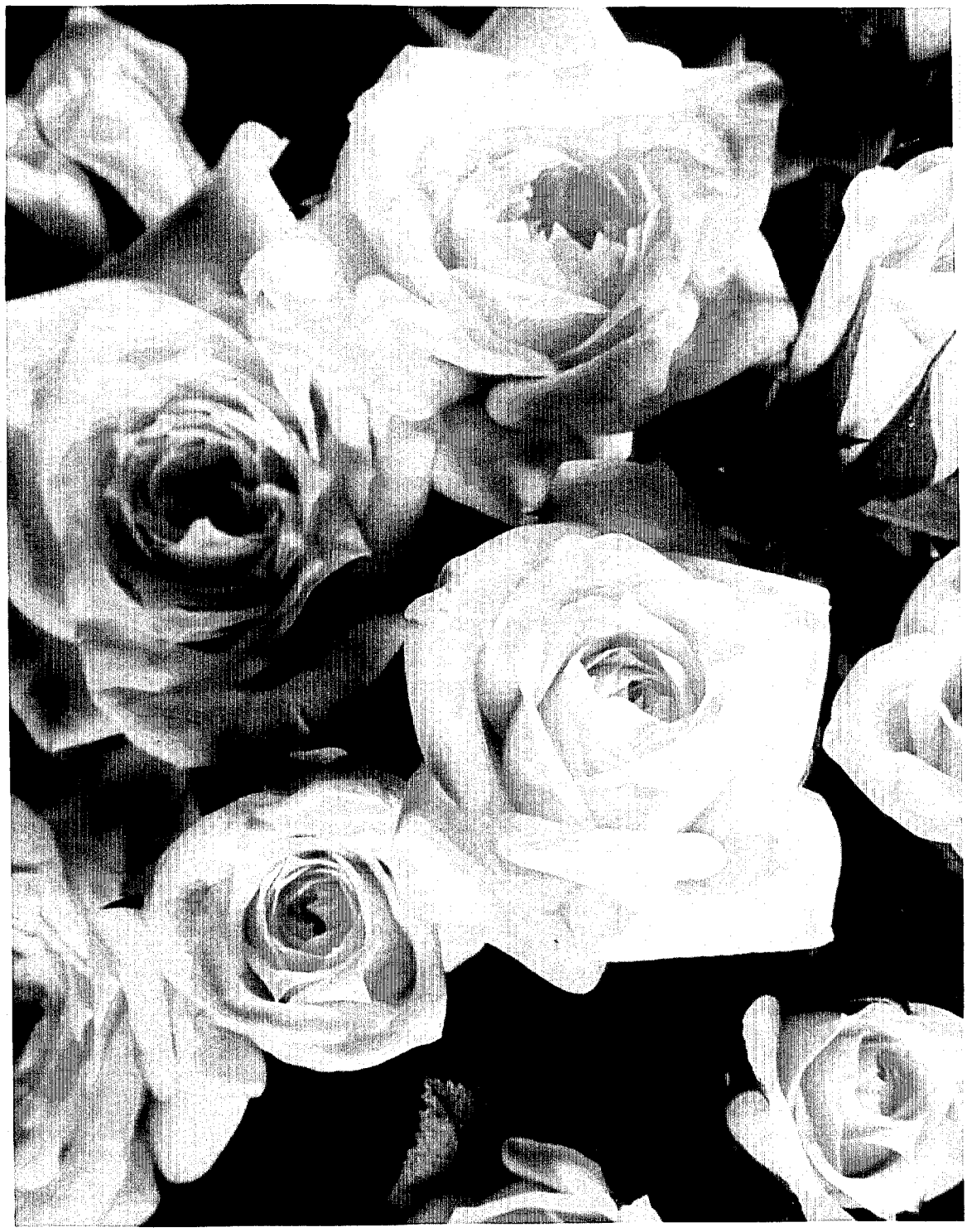

* * * * *